United States Patent
Crump et al.

(10) Patent No.: US 9,623,099 B2
(45) Date of Patent: Apr. 18, 2017

(54) SUBUNIT IMMERSION VACCINES FOR FISH

(71) Applicant: FVG LIMITED, Inverness (GB)

(72) Inventors: Elizabeth Mary Crump, Florham Park, NJ (US); Jan Burian, Florham Park, NJ (US); Joseph Michale Bricker, Florham Park, NJ (US); William Wayne Kay, Florham Park, NJ (US); Norman William Johnson, Florham Park, NJ (US)

(73) Assignee: FVG Limited, Inverness (GB)

( * ) Notice: Subject to any disclaimer, the term of this patent is extended or adjusted under 35 U.S.C. 154(b) by 0 days.

(21) Appl. No.: 14/431,349

(22) PCT Filed: Sep. 25, 2013

(86) PCT No.: PCT/US2013/061566
§ 371 (c)(1),
(2) Date: Mar. 26, 2015

(87) PCT Pub. No.: WO2014/052378
PCT Pub. Date: Mar. 4, 2014

(65) Prior Publication Data
US 2015/0343043 A1   Dec. 3, 2015

Related U.S. Application Data

(60) Provisional application No. 61/705,704, filed on Sep. 26, 2012.

(51) Int. Cl.
*A61K 39/02* (2006.01)
*A61K 39/12* (2006.01)
*A61K 39/00* (2006.01)

(52) U.S. Cl.
CPC .......... *A61K 39/02* (2013.01); *A61K 39/0208* (2013.01); *A61K 39/0216* (2013.01); *A61K 39/12* (2013.01); *A61K 2039/54* (2013.01); *A61K 2039/552* (2013.01); *A61K 2039/70* (2013.01); *C12N 2720/10034* (2013.01)

(58) Field of Classification Search
CPC .......... A61K 2039/54; A61K 2039/552; A61K 2039/70; A61K 39/02; A61K 39/0216; A61K 39/12; C12N 2720/10034
See application file for complete search history.

(56) References Cited

U.S. PATENT DOCUMENTS

2003/0072772 A1*  4/2003  Vakharia ................ A61K 39/12
424/205.1

FOREIGN PATENT DOCUMENTS

WO    02/38770 A1    5/2002

OTHER PUBLICATIONS

Huising et al. Vaccine 21: 4178-4193, Oct. 1, 2003.*
Dumetz et al. Appl. Environ. Microbiol. 72: 4845-4852, 2006.*
Edgington. Biotechnology 13: 1442-1444, 1995.*
Woo PTK. Parassitologia 49: 185-191, 2007.*
Skolnick et al. Trends in Biotechnology 18: 34-39, 2000.*
Greenspan et al. Nature Biotechnology 17:936-937, 1999.*
Huising et al., "Increased efficacy of immersion vaccination in fish with hyperosmotic pretreatment," Vaccine, 21: 4178-4193 (2003).
Allnutt et al., "Antigenicity of infectious pancreatic necrosis virus VP2 subviral particles expressed in yeast," Vaccine, 25: 4880-4888 (2007).
Sommerset et al., "Vaccines for fish in aquaculture," Expert Rev. Vaccines, 4(1): 89-101 (2005).
Shoemaker et al., "Efficacy of a modified live Flavobacterium columnare vaccine in fish," Fish Shellfish Immunol., 30 (1):304-308 (2011).
Shivappa et al., "Development of a subunit vaccine for infectious pancreatic necrosis virus using a baculovirus insect/larvae system," Developments in biologicals, 121:165-74 (2005).

* cited by examiner

*Primary Examiner* — S. Devi

(74) *Attorney, Agent, or Firm* — Morgan, Lewis & Bockius LLP

(57) ABSTRACT

The present disclosure provides an immersion vaccine for fish comprising at least one isolated antigen, specifically a recombinant antigen, such as is *F. psychrophilum* and/or infectious pancreatic necrosis virus (IPNV).

6 Claims, No Drawings

SUBUNIT IMMERSION VACCINES FOR FISH

A computer readable text file, entitled "SequenceListing.txt," created on or about 3 Oct. 2016 with a file size of about 14 kb contains the sequence listing for this application and is hereby incorporated by reference in its entirety.

FIELD OF THE INVENTION

This invention relates to the field of subunit immersion vaccines to protect fish from disease caused by infectious pathogens. In particular, the invention pertains to the field of immersion vaccines comprising recombinant antigens to protect fish from disease caused by Flavobacteriaceae and/or infectious pancreatic necrosis virus (IPNV).

BACKGROUND OF THE INVENTION

The industrial cultivation of fish through aquaculture is expanding dramatically. Infectious diseases caused by pathogens constitute a major problem that the industrial aquatic establishments must overcome. To prevent the onset of these infectious diseases, the recurrent strategy is the application of vaccines. Nearly all of the vaccines currently in use in aquaculture correspond to live-attenuated or inactivated cultures of the same pathogenic organism that produces the disease. Recombinant vaccines are increasingly growing at the research laboratory level, but field application is still almost exclusively through injection techniques.

There are two ways in which fish can be vaccinated: the vaccines can be applied by injection or by immersion. At present, one of the biggest problems in aquaculture is that the injectable vaccines are difficult and expensive to administer, and generally cannot be used in young weighing less than 15-20 grams due both to the risk of producing intraperitoneal adhesions and to the production of high dispersion in fish sizes at harvesting. Additionally, use of injectable vaccines causes stress in the fish, high cost of labor, and risk of accidents from inadvertent injections to the users.

In spite of the potential advantages of immersion vaccines, it has been the injectable vaccines that have had a greater development in commercial aquaculture. The intraperitoneal injection of fish is currently the most common method to administer vaccines, principally due to its high efficiency and meticulous dosing that guarantees adequate plasma levels. Current immersion vaccines are often characterized by their inefficient absorption through the fish's skin and can suffer from reduced immunogenicity. As a result, highly immunogenic compositions such as live-attenuated or inactivated pathogens are generally required.

*Flavobacterium psychrophilum* is a gram-negative bacterial fish pathogen that causes bacterial coldwater disease (CWD), and is considered to be an important pathogen affecting salmonid aquaculture due to its wide distribution and economic impact. In the United States, it is estimated that annual losses incurred from CWD in the Pacific Northwest alone are approximately 9.6 and 4 million dollars for commercial aquaculture of rainbow trout (*Oncorhynchus mykiss* Walbaum) and conservation aquaculture of salmonid species, respectively.

*Flavobacterium columnare* is an aquatic bacterium that is highly infectious for both warm and cold water species of fish. In the channel catfish (*Ictalurus punctatus*), it is the causative agent of columnaris disease. *Flavobacterium columnare* is a Gram-negative, rod shaped, pathogen that has been isolated from channel catfish in areas of the southeastern United States where this species is cultured. The disease also affects sports fish (i.e., walleye and largemouth bass) and aquarium fishes. Medicated feed (antibiotics) is currently used to try to control this bacterial infection. However, these treatments are limited in their effectiveness, and most producers have discontinued use of medicated feeds. Prevention of columnaris disease by vaccination is an important goal, and a top priority of catfish and other fish producers throughout the world. Estimated savings to these industries would be in excess of $100 million annually.

Treatment options for *Flavobacterium* are limited, and include reducing pathogen concentrations, eliminating the spread of the pathogen, and the use of antibiotics. However, the effectiveness of treatment is usually inconsistent, and there are potential risks of developing antibiotic-resistant strains. Therefore, a vaccine to prevent infection is desired.

Infectious pancreatic necrosis virus (IPNV) is the causal agent of a highly contagious and destructive disease of Rainbow and Brook trout and Atlantic salmon. Highly virulent strains of IPNV may cause greater than 90% mortality in hatchery stocks less than four months old. Survivors of infection can remain lifelong asymptomatic carriers and serve as reservoirs of infection, shedding virus in their feces and reproductive products. Therefore, IPNV is a pathogen of major economic importance to the aquaculture industry.

IPNV is the prototype of the Birnaviridae virus family. IPNV contains a bisegmented dsRNA genome, which is surrounded by a single-shelled icosahedral capsid. The larger of the two genome segments, segment A (3097 bases), encodes a 106-kDa precursor polyprotein which is processed to yield mature viral structural proteins VP2 and VP3, and VP4 (also named NS) a non-structural protein (Duncan et al. 1987). VP2 has been identified as the major host protective antigen of IPNV.

An ideal vaccine for IPNV must induce protection at an early age, prevent carrier formation, and should be effective against a large number of IPNV subtypes. Inactivated IPNV vaccines have been found to be efficacious by intraperitoneal inoculation IPNV (described in US2003072772 and U.S. Pat. No. 8,168,201, hereby incorporated by reference); however, they are not efficient and result in additional dosing through injection. U.S. Pat. No. 8,168,201 describes antigenic compositions comprising particular antigens as subunit vaccines wherein the vaccines can further comprise additional promiscuous T-cell epitopes.

*Tenacibaculum maritimum* (formerly, *Cytophaga marina*, *Flexibacter marinus* and *F. maritimus*) is the causative agent of flexibacteriosis in marine fish and belongs to the Flavobacteriaceae family of bacteria (Wakabayashi et al., 1986; Bernardet and Grimont, 1989; Sukui et al., 2001). Marine flexibacteriosis is widely distributed in cultured and wild fish in Europe, Japan, North America and Australia (McVicar and White, 1979, 1982). Among the cultured fish, the disease has been reported in turbot, sole, gilthead seabream, seabass, red seabream, black seabream (Acanthopagrus schlegeli), flounder and salmonids.

Although both adults and juveniles may be affected by marine flexibacteriosis, younger fish suffer a more severe form of the disease. An increased prevalence and severity of the disease has been reported at higher temperatures. In addition to water temperature, the disease is influenced by a multiplicity of environmental (stress) and host-related factors (skin surface condition). In general, the affected fish have an eroded and haemorrhagic mouth, ulcerative skin lesions, frayed fins and tail rot. A systemic disease can be also established involving different internal organs. The loss of epithelial fish surface, typical of this disease, is also a portal of entry for other bacterial or parasitic pathogens.

In order to be commercially useful, a vaccine for fish must be capable of conferring protective immunity against a pathogen when the vaccine is administered by practical methods, such as immersing the fish in water containing the vaccine. Vaccination protocols that require individual handling of fish, such as by injection, are not practical for many commercial aquaculture operations.

U.S. Patent Publication 2008/0317781 to Cain et al. provides that "immunization with killed bacteria has been attempted with *F. psychrophilum*, and protection obtained by immersion or by injection with the killed bacteria has been minimal." Consequently, Cain et al. produced a novel live attenuation process for *F. psychrophilum* that purportedly produced effective immunization through immersion techniques.

To date, no effective commercial immersion vaccines exist based on subunit antigens, however, particularly with recombinant antigens. In view of the concerns raised by Cain et al. relating to the difficulty producing immunogenic immersion vaccines with killed bacteria, subunit immersion vaccines would presumably face even greater challenges. Against this backdrop, Applicants approached the difficult task of developing a subunit immersion vaccine.

SUMMARY OF THE INVENTION

Surprisingly, Applicants have discovered that subunit antigens can in fact be used in immersion vaccines to protect fish against both bacterial and viral infections. Accordingly, one embodiment of the present invention provides an immersion vaccine for fish comprising at least one isolated antigen. More particularly, the antigen is a recombinant antigen.

In another embodiment, the antigen is from bacteria. More particularly, the antigen is from a Flavobacteriaceae. More particular still, the Flavobacteriaceae is selected from the group consisting of *Flavobacterium columnare* (*F. columnare*), *Flavobacterium psychrophilum* (*F. psychrophilum*) and *Tenacibaculum maritimum* (*T. maritimum*). In another embodiment, the Flavobacteriaceae is *F. psychrophilum*. In another embodiment, said vaccine cross-protects against at least one of *F. columnare* and/or *T. maritimum*.

In another embodiment, the isolated antigen is a histone-like protein. In another embodiment, the antigen has at least 70% identity to the amino acid sequence of SEQ ID NO: 2, SEQ ID NO: 4, SEQ ID NO: 6 or SEQ ID NO: 7. In another embodiment, the antigen comprises a protein or polypeptide having the amino acid sequence of SEQ ID NO: 2, SEQ ID NO: 4, SEQ ID NO: 6 or SEQ ID NO:7 or an amino sequence having 50%, 60%, 70%, 75%, 80%, 85%, 90%, 95%, 96%, 97%, 98%, 99%, 99.5% identity thereto, or a fragment thereof. In another embodiment, the antigen is fused with a T-cell epitote. In another embodiment, the antigen is encoded by a nucleotide sequence of SEQ ID NO: 1, SEQ ID NO: 3 or SEQ ID NO: 5 or a nucleotide sequence having 50%, 60%, 70%, 75%, 80%, 85%, 90%, 95%, 96%, 97%, 98%, 99%, 99.5% identity thereto.

In another embodiment, the antigen is from a virus. More particularly, the antigen is from infectious pancreatic necrosis virus (IPNV). More particular still, the IPNV antigen is a VP2 protein. In some embodiments, the VP2 protein is an isolated recombinant antigen that can be a fragment of the full length VP2 protein. In some embodiments, the recombinant VP2 antigen has at least 70% identity to the amino acid sequence of SEQ ID NO: 8. In another embodiment, the antigen comprises a protein or polypeptide having the amino acid sequence of SEQ ID NO: 8 or an amino sequence having 50%, 60%, 70%, 75%, 80%, 85%, 90%, 95%, 96%, 97%, 98%, 99%, 99.5% identity thereto, or a fragment thereof.

In another embodiment, the composition comprises at least two different isolated antigens. More particularly, at least two isolated antigens are an IPNV antigen and a *F. psychrophilum* antigen. In one embodiment, the composition comprises two isolated antigens in a fusion protein as in SEQ ID NO: 9 or an amino acid sequence homologous to SEQ ID NO: 9.

In another embodiment, the vaccine consists essentially of recombinant antigens. In another embodiment, the vaccine does not contain live-attenuated or inactivated pathogens.

Another embodiment of the invention provides at least one additional agent. More particularly, the at least one additional agent is a bacterin or live attenuated or inactivated virus. In another embodiment, at least one additional agent is an adjuvant. In another embodiment, the additional agent is selected from the group consisting of *Aeromonas hydrophile, Aeromonas salmonicida, Pseudomonas fluorescens, Vibrio anguillarum, Vibrio salmonicida, Renibacterium salmoninarum*, infectious haemopoietic necrosis virus (IHNV), infectious salmon anemia virus (ISAV), pancreas disease virus (PDV) in particular, salmon alphavirus (SAV), salmon poxvirus, and viral haemorrhagic septicemia virus (VHSV).

Another embodiment of the invention provides a method for immunizing a fish against a pathogen comprising immersing the fish in a vaccine as described herein. More particularly, the vaccine comprises a recombinant *F. psychrophilum* antigen and a recombinant IPNV antigen.

Another embodiment provides for the manufacture of a medicament comprising the immersion vaccine for treatment or prevention of infection from a fish pathogen.

These and other embodiments, features, and advantages of the invention will become apparent from the detailed description and the appended claims set forth herein below. It is understood that each of the foregoing and following embodiments can be combined into a single embodiment.

BRIEF DESCRIPTION OF THE SEQUENCE LISTING

SEQ ID NO: 1 Is the nucleotide sequence encoding the Histone Like Protein (HLP) from *T. maritimum.*

SEQ ID NO: 2 Is the amino acid sequence for the Histone Like Protein (HLP) from *T. maritimum* encoded in SEQ ID NO: 1. The amino acid sequence can be fused with a T-cell epitope to enhance immunogenicity.

SEQ ID NO: 3 Is the nucleotide sequence encoding the Histone Like Protein (HLP) from *F. columnare.*

SEQ ID NO: 4 Is the amino acid sequence for the Histone Like Protein (HLP) from *F. columnare* encoded in SEQ ID NO: 3. The amino acid sequence can be fused with a T-cell epitope to enhance immunogenicity.

SEQ ID NO: 5 Is the nucleotide sequence encoding the Histone Like Protein (HLP) from *F. psychrophilum.*

SEQ ID NO: 6 Is the amino acid sequence for the Histone Like Protein (HLP) from *F. psychrophilum* encoded in SEQ ID NO: 5. The amino acid sequence can be fused with a T-cell epitope to enhance immunogenicity.

SEQ ID NO: 7 Is the amino acid sequence of recombinant *F. psychrophilum* antigen CM8. The N-terminus leading peptide C is followed with measles epitope (M) and the carboxy end of the sequence is the *F. psychrophilum* protein.

SEQ ID NO: 8 Is the protein expressed from the CTMVP2c expression cassette which consists of (amino-carboxy sequence) the N-terminal Protein C, the immunostimulatory Measles Virus Fusion protein epitope and Tetanus toxin protein epitope and the VP2 sequence fragment used in the Examples described herein.

SEQ ID NO: 9 Is the amino acid sequence of the rHLP-/rIPNV VP2 fusion protein used in the Examples described herein.

DETAILED DESCRIPTION OF THE INVENTION

The definitions below apply to this disclosure. They supersede any contradictory definitions contained in each individual reference incorporated herein by reference. Words not defined have the meaning commonly used by one skilled in the art. Further, unless otherwise required by context, singular terms shall include pluralities, and plural terms shall include the singular.

"About" or "approximately," when used in connection with a measurable numerical variable, refers to the indicated value of the variable and to all values of the variable that are within the experimental error of the indicated value (e.g., within the 95% confidence interval for the mean), or within 10% of the indicated value, whichever is greater. If "about" is used in reference to time intervals in weeks, "about 3 weeks" is 17 to 25 days, and "about 2 to about 4 weeks" is 10 to 40 days.

"Adjuvant", as used herein, refers to any substance which serves as a non-specific stimulator of the immune response. See below for a further description of adjuvants.

"Amino acid", as used herein, refers to naturally-occurring and synthetic amino acids, as well as amino acid analogs and amino acid mimetics that function in a manner similar to naturally-occurring amino acids. Naturally-occurring amino acids are those encoded by the genetic code, as well as those amino acids that are later modified, for example, hydroxyproline, carboxyglutamate, and O-phosphoserine. Stereoisomers (e.g., D-amino acids) of the twenty conventional amino acids, unnatural amino acids such as α and α-disubstituted amino acids, N-alkyl amino acids, and other unconventional amino acids, may also be suitable components for polypeptides of the present invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids. Amino acids may be referred to herein by either their commonly known three-letter symbols or their one-letter symbols recommended by the IUPAC-IUB Biochemical Nomenclature Commission. "Antibody", as used herein, is any polypeptide comprising an antigen-binding site regardless of the source, method of production, or other characteristics. It refers to an immunoglobulin molecule or a fragment thereof that specifically binds to an antigen as the result of an immune response to that antigen. Immunoglobulins are serum proteins composed of "light" and "heavy" polypeptide chains having "constant" and "variable" regions and are divided into classes (e.g., IgA, IgD, IgE, IgG, and IgM) based on the composition of the constant regions. In mammals and birds, the immunoglobulin M (IgM), IgG and IgY isotypes have a predominant role in systemic responses, whereas IgA is the key participant in mucosal surfaces. Teleost fish are the most primitive bony vertebrates that contain immunoglobulins and, in contrast to mammals and birds, serum IgM in most teleosts is expressed as a tetramer, although IgM monomers have been described. In addition teleosts are devoid of IgA or a functional equivalent of IgA although recent research have added two new immunoglobulin molecules, IgD and IgT/IgZ, with IgT being reported as an immunoglobulin specialized in gut mucosal immunity. An antibody that is "specific" for a given antigen indicates that the variable regions of the antibody recognize and bind a specific antigen exclusively. The term includes, but is not limited to: a polyclonal antibody, a monoclonal antibody, a monospecific antibody, polyspecific antibody, humanized antibody, a tetrameric antibody, a tetravalent antibody, a multispecific antibody, a single chain antibody, a domain-specific antibody, a single domain antibody, a domain-deleted antibody, a fusion protein, an ScFc fusion protein, a single-chain antibody, chimeric antibody, synthetic antibody, recombinant antibody, hybrid antibody, mutated antibody, and CDR-grafted antibodies. Antibodies can be intact immunoglobulins derived from natural sources or from recombinant sources, or can be immunoreactive portions of intact immunoglobulins. An "antibody" can be converted to an antigen-binding protein, which includes but is not limited to antibody fragments which include but are not limited to: Fab, F(ab')$_2$, an Fab' fragment, an Fv fragment, a single-chain Fv (ScFv) fragment, an Fd fragment, a dAb fragment, diabodies, a CDR3 peptide, a constrained FR3-CDR3-FR4 peptide, a nanobody, a bivalent nanobody, a small modular immunopharmaceutical (SMIPs), and a minibody and any of above mentioned fragments and their chemically or genetically manipulated counterparts, as well as other antibody fragments that retain antigen-binding function. Typically, such fragments would comprise an antigen-binding domain. As will be recognized by those of skill in the art, any of such molecules may be engineered (for example "germlined") to decrease its immunogenicity, increase its affinity, alter its specificity, or for other purposes.

"Antigen" or "immunogen", as used herein, refers to a molecule that contains one or more epitopes (linear, conformational or both) that upon exposure to a subject will induce an immune response that is specific for that antigen. An epitope is the specific site of the antigen which binds to a T-cell receptor or specific antibody, and typically comprises about 3 amino acid residues to about 20 amino acid residues. The term antigen refers to subunit antigens—antigens separate and discrete from a whole organism with which the antigen is associated in nature—as well as whole killed, attenuated or inactivated bacteria, viruses, fungi, parasites or other microbes. The term antigen also refers to antibodies, such as anti-idiotype antibodies or fragments thereof, and to synthetic peptide mimotopes that can mimic an antigen or antigenic determinant (epitope). The term antigen also refers to an oligonucleotide or polynucleotide that expresses an antigen or antigenic determinant in vivo, such as in DNA immunization applications.

"Antigenicity", as used herein, refers to the capability of a protein or polypeptide to be immunospecifically bound by an antibody raised against the protein or polypeptide.

"Buffer" means a chemical system that prevents change in the concentration of another chemical substance. Proton donor and acceptor systems serve as buffers, preventing marked changes in hydrogen ion concentration (pH). A further example of a buffer is a solution containing a mixture of a weak acid and its salt (conjugate base), or a weak base and its salt (conjugate acid).

The term "cell line" or "host cell", as used herein, means a prokaryotic or eukaryotic cell in which a virus can replicate or be maintained.

The term "culture", as used herein, means a population of cells or microorganisms growing in the absence of other species or types.

"Dose" refers to a vaccine or immunogenic composition given to a subject. A "first dose" or "priming dose" refers to the dose of such a composition given on Day 0. A "second dose" or a "third dose" or an "annual dose" refers to an amount of such composition given subsequent to the first dose, which can be but is not required to be the same vaccine or immunogenic composition as the first dose.

An "epitope" is the specific site of the antigen which binds to a T-cell receptor or specific antibody, and typically comprises from about 3 amino acid residues to about 20 amino acid residues.

"Excipient", as used herein, refers to a non-reactive carrier component of a vaccine or immunogenic composition that is not an antigen. Preferred excipients are those known in the art for immersion vaccines.

The term "fish" refers to both cold and warm water fish that can be treated by the vaccine compositions of the present invention. Fish that may be treated by the method of the invention include any fish that is susceptible to infection and disease caused by the particular organism or pathogen. The fish may be a marine or salt-water fish. Examples of suitable fish for the method of invention include salmonids (*Oncorhynchus* sp. and *Salmo* sp.), American, European, and Japanese eels (*Anguilla* sp.), tilapia (*Oreochromis* sp.), striped bass and hybrid-striped bass (*Morone chrysops* and *M. saxatilis*), flounders (*Seriola* sp.), seabream (*Sparus* sp.), sea perch (*Lates calcarifer*), the estuarine grouper (*Epinephelus tawine*), walleye (*Stitzostedion vitreum*), channel catfish (*Ictalurus punctutus*), centrachids (such as largemouth bass, *Micropterus salmoides*), brown bullheads (*Nebulosus* sp.), fat head minnows (*Pimephales promelas*), golden shiners (*Netemigonus crysoleucas*), carp (*Cyprinus carpio*), all species of tuna, aquarium fish species such as black mollies (*Poecilia sphenops*), platies (*Xiphophorus maculatus*), sea lamprey (*Petromyzon marinus*), tench (*Tinca tinca*), crucian carp (*Carassius carassius*), goldfish (*Carassius auratus*), sweetfish (*Plecoglossus altivelis*), freshwater minnows (*Zacco platypus*), as well as perch (*Perca fluviatilis*), roach (*Rutilus rutilus*) and sea bass (*Serranidae* sp.) In a preferred embodiment, the fish are used in aquaculture.

"Fragment" refers to a truncated portion of a protein or gene. "Functional fragment" and "biologically active fragment" refer to a fragment that retains the biological properties of the full length protein or gene.

"Homology" or "percent homology" refers to the percentage of nucleotide or amino acid residues in the candidate sequence that are identical or similar with the residues in the comparator sequence(s) after aligning the sequences and introducing gaps, if necessary, to achieve the maximum percent sequence homology, and also considering any conservative substitutions as part of the sequence homology. In a preferred aspect, polynucleotides or amino acid sequences provided herein have greater than about 60% sequence homology, greater than about 70% sequence homology, greater than about 80% sequence homology, greater than about 90% sequence homology, greater than about 95% sequence homology, greater than about 96% sequence homology, greater than about 97% sequence homology, greater than about 98% sequence homology, or greater than about 99% sequence homology.

"Identity" or "percent identity" refers to the percentage of nucleotides or amino acids in the candidate sequence that are identical with the residues in the comparator sequence after aligning both sequences and introducing gaps, if necessary, to achieve the maximum percent sequence identity, and not considering any conservative substitutions as part of the sequence identity. In a preferred aspect, polynucleotides or amino acid sequences provided herein have, to the reference sequence (e.g. SEQ ID NO: 2, 4, or 6) greater than about 60% sequence identity, greater than about 70% sequence identity, greater than about 80% sequence identity, greater than about 90% sequence identity, greater than about 95% sequence identity, greater than about 96% sequence identity, greater than about 97% sequence identity, greater than about 98% sequence identity, or greater than about 99% sequence identity.

"Immersion vaccine" relates to a solution or a pre-mix for a solution that surrounds, encompasses or coats the surface of a fish and results in vaccination against a particular pathogen. Immersion vaccines include dip vaccines, where fish are briefly dipped in a solution, and bath vaccines, where fish are immersed in solution for a period of time, such as hours or even days.

"Immune response", as used herein, in a subject refers to the development of a humoral immune response, a cellular immune response, or a humoral and a cellular immune response to an antigen. A "humoral immune response" refers to one that is at least in part mediated by antibodies. A "cellular immune response" is one mediated by T-lymphocytes or other white blood cells or both, and includes the production of cytokines, chemokines and similar molecules produced by activated T-cells, white blood cells, or both. Immune responses can be determined using standard immunoassays and neutralization assays, which are known in the art.

"Immunogenicity", as used herein, refers to the capability of a protein or polypeptide to elicit an immune response directed against a bacteria or virus that causes the identified disease.

An "immunogenic composition" is a preparation containing an immunogen, including, e.g., a protein, a peptide, a whole cell, inactivated, subunit or attenuated virus, or a polysaccharide, or combination thereof, administered to stimulate the recipient's humoral and cellular immune systems to one or more of the antigens present in the immunogenic composition. "Immunization" is the process of administering an immunogenic composition and stimulating an immune or immunogenic response to an antigen in a host. Preferred hosts are fish, such as fish used in aquacultre. Preferably, the immunogenic composition is a vaccine.

"Immunologically protective amount", as used herein, is an amount of an antigen effective to induce an immunogenic response in the recipient that is adequate to prevent or ameliorate signs or symptoms of disease, including adverse health effects or complications thereof. Either humoral immunity or cell-mediated immunity or both can be induced. The immunogenic response of an animal to a composition can be evaluated, e.g., indirectly through measurement of antibody titers, lymphocyte proliferation assays, or directly through monitoring signs and symptoms after challenge with wild type strain. The protective immunity conferred by a composition or vaccine can be evaluated by measuring, e.g., reduction of shed of challenge organisms, reduction in clinical signs such as mortality, morbidity, temperature, and overall physical condition, health and performance of the subject. The immune response can comprise, without limitation, induction of cellular and/or humoral immunity. The amount of a composition or vaccine that is therapeutically effective can vary, depending on the particular organism used, or the condition of the animal being treated or vaccinated, and can be determined by a veterinarian.

The term "isolated" refers to a substance that is either in substantially pure form, for example, greater than about 95% purity; or purified, enriched or removed in some way from its natural environment. Reference to "isolated" indicates an agent, such as a protein that is removed from its natural environment, such as from a host animal/fish, in a growth media, recombinantly produced, or purified from a whole cell bacterial preparation and may subsequently be added back to a composition comprising other actives or antigens. The term "isolated" encompasses immunogens that are in solution with other agents/diluents/excipients/adjuvants/proteins. Preferably, the vaccine compositions described herein are isolated.

"Medicinal agent" refers to any agent which is useful in the prevention, cure, or improvement of a medical condition, or the prevention of some physiological condition or occurrence.

"Monoclonal antibody", as used herein, refers to antibodies produced by a single line of hybridoma cells, all directed towards one epitope on a particular antigen. The antigen used to make the monoclonal antibody can be provided as an isolated protein of the pathogen or the whole pathogen. A "hybridoma" is a clonal cell line that consists of hybrid cells formed by the fusion of a myeloma cell and a specific antibody-producing cell. In general, monoclonal antibodies are of mouse origin. However, monoclonal antibody also refers to a clonal population of an antibody made against a particular epitope of an antigen produced by phage display technology, or method that is equivalent to phage display, or hybrid cells of non-mouse origin.

"Parenteral administration", as used herein, refers to the introduction of a substance, such as a composition or vaccine, into a subject's body through or by way of a route that does not include the digestive tract. Parenteral administration includes subcutaneous, intramuscular, intraarterial, and intravenous administration. For the purposes of this disclosure, parenteral administration excludes administration routes that primarily involve transport of the substance through mucosal tissue in the mouth, nose, trachea, and lungs.

The term "pathogen" or "pathogenic microorganism", as used herein, means a microorganism—for example *Flavobacterium columnare* (*F. columnare*), *Flavobacterium psychrophilum* (*F. psychrophilum*), *Tenacibaculum maritimum* (*T. maritimum*), and infectious pancreatic necrosis virus (IPNV)—which is capable of inducing or causing a disease, illness, or abnormal state in its host animal, preferably a disease affecting fish.

"Pharmaceutically acceptable" refers to substances which, within the scope of sound medical judgment, are suitable for use in contact with the tissues of subjects without undue toxicity, irritation, allergic response, and the like, commensurate with a reasonable benefit-to-risk ratio, and effective for their intended use.

"Polyclonal antibody", as used herein, refers to a mixed population of antibodies made against a particular pathogen or antigen. In general, the population contains a variety of antibody groups, each group directed towards a particular epitope of the pathogen or antigen. To make polyclonal antibodies, the whole pathogen, or an isolated antigen, is introduced by inoculation or infection into a host, which induces the host to make antibodies against the pathogen or antigen.

The term "polynucleotide", as used herein, means an organic polymer molecule composed of nucleotide monomers covalently bonded in a chain. DNA (deoxyribonucleic acid) and RNA (ribonucleic acid) are examples of polynucleotides with distinct biological function.

The term "polypeptide", as used herein, means an organic polymer molecule composed of two or more amino acids bonded in a chain.

"Preventing infection", as used herein, means to prevent or inhibit the replication of the bacteria or virus which cause the identified disease, to inhibit transmission of the bacteria or virus, to prevent the bacteria or virus from establishing itself in its host, or to alleviate the symptoms of the disease caused by infection. The treatment is considered therapeutic if there is a reduction in bacterial or viral load.

"Protection", "protecting", "protective immunity", and the like, as used herein with respect to a vaccine or other composition, means that the vaccine or composition prevents or reduces the symptoms of the disease caused by the organism from which the antigen(s) used in the vaccine or composition is derived. The terms "protection", "protecting", and the like, also mean that the vaccine or composition can be used to "treat" the disease, or one or more symptoms of the disease that already exists in a subject.

"Relative Percent Survival" (RPS) can be defined or computed as follows: RPS={1−(% vaccinate mortality/% control mortality)}×100.

"Respiratory administration", as used herein, refers to the introduction of a substance, such as a vaccine or other composition, into a subject's body through or by way of inhalation of a nebulized (atomized) substance. In respiratory administration, the primary transport mechanism involves absorption of the atomized substance through the mucosa in the trachea, bronchi, and lungs and is therefore different than intranasal or peroral administration.

The terms "specific binding," "specifically binds," and the like, are defined as two or more molecules that form a complex that is measurable under physiologic or assay conditions and is selective. An antibody or other inhibitor is said to "specifically bind" to a protein if, under appropriately selected conditions, such binding is not substantially inhibited, while at the same time non-specific binding is inhibited. Specific binding is characterized by high affinity and is selective for the compound or protein. Nonspecific binding usually has low affinity. Binding in IgG antibodies, for example, is generally characterized by an affinity of at least about $10^{-7}$ M or higher, such as at least about $10^{-8}$ M or higher, or at least about $10^{-9}$ M or higher, or at least about $10^{-10}$ or higher, or at least about $10^{-11}$ M or higher, or at least about $10^{-12}$ M or higher. The term is also applicable where, e.g., an antigen-binding domain is specific for a particular epitope that is not carried by numerous antigens, in which case the antibody carrying the antigen-binding domain will generally not bind other antigens.

"Specific immunogenic fragment", as used herein, refers to a portion of a sequence that is recognizable by an antibody or T cell specific for that sequence.

"Subject", as used herein, refers to any animal having an immune system, preferably fish.

"Substantially identical", as used herein, refers to a degree of sequence identity of at least about 90%, at least about 95%, at least about 96%, at least about 97%, at least about 98%, or at least about 99%.

"Subunit vaccine", and "subunit composition", as used herein, refers to a type of vaccine or composition that includes one or more antigens—but not all antigens—which are derived from or homologous to, antigens from a pathogen of interest, such as a virus, bacterium, parasite, fungus, or fungal-like organism. Such a composition or vaccine is substantially free of intact pathogen cells or pathogenic particles, or the lysate of such cells or particles. Thus, a subunit vaccine or subunit composition can be prepared from at least partially purified, or substantially purified, immunogenic polypeptides from the pathogen or their analogs. Methods of obtaining an antigen or antigens in the subunit vaccine or subunit composition include standard purification techniques, recombinant production, or chemical synthesis. A "subunit vaccine" or "subunit composition" thus refers to a vaccine or composition consisting of a defined antigenic component or components of a virus, bacterium, or other immunogen. The subunit component of the present invention can be recombinantly produced and can comprise IPNV VP2 antigen and/or *F. psychrophilum* antigen.

A "T-Cell epitope" as used herein refers to an antigen or antigenic fragment capable of enhancing a t-cell response in a target organism. Specific T-Cell epitopes as used herein are described in U.S. Pat. No. 8,168,201 (referred to as "promiscuous T-cell epitopes" or "PTCE" therein), the contents of which are hereby incorporated by reference as if set forth fully herein. In particular, the T-Cell epitope sequences of U.S. Pat. No. 8,168,201, which are designated as SEQ ID NO: 1, 2, 3, 4, 5, 6 and 7, therein are hereby incorporated herein. Those sequences may be conjugated or fused to any of the amino acid sequences listed in the present application to form an immunogenic composition or antigen of the present invention.

"$TCID_{50}$" refers to "tissue culture infective dose" and is defined as that dilution of a virus required to infect 50% of a given batch of inoculated cell cultures. Various methods can be used to calculate $TCID_{50}$, including the Spearman-Karber method, which is utilized throughout this specification. For a description of the Spearman-Karber method, see B. W. Mahy & H. O. Kangro, Virology Methods Manual 25-46 (1996).

"Therapeutic agent", as used herein, refers to any molecule, compound, virus or treatment, preferably a virus attenuated or killed, or subunit or compound, that assists in the treatment of a viral, bacterial, parasitic or fungal infection, disease or condition caused thereby.

"Therapeutically effective amount", as used herein, refers to an amount of an antigen or vaccine or composition that would induce an immune response in a subject (e.g., fish) receiving the antigen or vaccine or composition which is adequate to prevent or ameliorate signs or symptoms of disease, including adverse health effects or complications thereof, caused by infection with a pathogen, such as a virus, bacterium, parasite, fungus, or fungal-like organism. Humoral immunity or cell-mediated immunity, or both humoral and cell-mediated immunity, can be induced. The immunogenic response of an animal to an antigen, vaccine, or composition can be evaluated indirectly through measurement of antibody titers, lymphocyte proliferation assays, or directly through monitoring signs and symptoms after challenge with the wild type strain. The protective immunity conferred by a vaccine or composition can be evaluated by measuring reduction of challenge organism shed, and/or reduction in clinical signs, such as mortality, morbidity, temperature, and overall physical condition, health, and performance of the subject. The amount of a vaccine or composition that is therapeutically effective can vary, depending on the particular immunogen used, or the condition of the subject, and can be determined by one skilled in the art.

"Treat" or "treating", as used herein, refers to reversing, alleviating, inhibiting the progress of, or preventing a disorder, condition or disease to which such term applies, or to preventing one or more symptoms of such disorder, condition or disease.

"Vaccine" or "vaccine composition," as used herein, refers to an immunogenic composition selected from a virus or bacteria, preferably in isolated subunit form. Administration of the vaccine to a subject results in an immune response. The vaccine can be introduced directly into the subject by any known route of administration, preferably through immersion. The terms mean a composition which prevents or reduces an infection, or which prevents or reduces one or more signs or symptoms of infection. The protective effects of a vaccine composition against a pathogen are normally achieved by inducing in the subject an immune response. Generally speaking, abolished or reduced incidences of infection, amelioration of the signs or symptoms, or accelerated elimination of the microorganism from the infected subjects are indicative of the protective effects of a vaccine composition.

Antigens, Immunogenic Compositions, and Vaccines

The present disclosure is based upon the unexpected discovery that inclusion of isolated antigens in immersion vaccines results in substantially improved efficacy, efficiency and safety. That is, when administered to a fish prior to pathogenic challenge, the composition prevents the onset of disease, and does not result in adverse side-effects.

Viruses encompassed by the present invention can be propagated in cells, cell lines and host cells. Said cells, cell lines or host cells can be for example, but not limited to, mammalian cells and non-mammalian cells, including insect and plant cells. Cells, cell lines, and host cells in which viruses encompassed by the present invention can be propagated are readily known, and accessible to those of ordinary skill in the art.

Bacteria encompassed by the present invention can be cultured and propagated using various culture media known to those of ordinary skill in the art, including both broth (liquid) and agar (solid; semi-solid) cultivation media. Some bacteria can also be cultured and propagated in mammalian cells or non-mammalian cells.

The viruses and bacteria encompassed by the present invention can be attenuated or inactivated prior to use in an immunogenic composition or vaccine. Methods of attenuation and inactivation are well known to those skilled in the art. Methods for attenuation include, but are not limited to, serial passage in cell culture on a suitable cell line (viruses and some bacteria), serial passage in broth culture (bacteria), ultraviolet irradiation (viruses and bacteria), and chemical mutagenesis (viruses and bacteria). Methods for viral or bacterial inactivation include, but are not limited to, treatment with formalin, betapropriolactone (BPL) or binary ethyleneimine (BEI), or other methods known to those skilled in the art.

Inactivation by formalin can be performed by mixing the suspension containing the microorganism with 37% formaldehyde to a final formaldehyde concentration of 0.5%. The microorganism-formaldehyde mixture is mixed by constant stirring for approximately 24 hours at room temperature. The inactivated microorganism mixture is then tested for residual live organisms by assaying for growth on a suitable cell line or broth media.

For some antigens, inactivation by BEI can be performed by mixing the suspension containing the microorganism of the present invention with 0.1 M BEI (2-bromo-ethylamine in 0.175 N NaOH) to a final BEI concentration of 1 mM. For other antigens, the final BEI concentration is 2 mM. One skilled in the art would know the appropriate concentration to use. The virus-BEI mixture is mixed by constant stirring for approximately 48 hours at room temperature, followed by the addition of 1.0 M sodium thiosulfate to a final concentration of 0.1 mM. Mixing is continued for an additional two hours. The mixture containing the inactivated microorganism is tested for residual live virus by assaying for growth on a suitable cell line or broth media.

Immunogenic compositions and vaccines encompassed by the present invention can include one or more pharmaceutically-acceptable carriers, which includes any and all solvents, dispersion media, coatings, adjuvants, stabilizing agents, diluents, preservatives, antibacterial and antifungal agents, isotonic agents, adsorption delaying agents, and the like. Diluents can include water, saline, dextrose, ethanol, glycerol, and the like. Isotonic agents can include sodium chloride, dextrose, mannitol, sorbitol, and lactose, among others known to those skilled in the art. Stabilizers include albumin, among others known to the skilled artisan. Preservatives include merthiolate, among others known to the skilled artisan.

Specific agents that may be added to the immersion vaccines described herein, include *Aeromonas hydrophile, Aeromonas salmonicida, Pseudomonas fluorescens, Vibrio anguillarum, Vibrio salmonicida, Renibacterium salmoninarum*, infectious haemopoietic necrosis virus (IHNV), infectious salmon anemia virus (ISAV), pancreas disease virus (PDV) in particular, salmon alphavirus (SAV), salmon poxvirus, and viral haemorrhagic septicemia virus (VHSV).

Adjuvants, which can be included in the vaccines described herein can be metabolizable, referring to adjuvants consisting of components that are capable of being metabolized by the target species such as vegetable oil based adjuvants. A metabolizable adjuvant can be a metabolizable oil. Metabolizable oils are fats and oils that typically occur in plants and animals, and usually consist largely of mixtures of triacylglycerols, also known as triglycerides or neutral fats. These nonpolar, water insoluble substances are fatty acid triesters of glycerol. Triacylglycerols differ according to the identity and placement of their three fatty acid residues or side chains.

The adjuvant can also be non-metabolizable, referring to adjuvants consisting of components that cannot be metabolized by the body of the animal subject to which the emulsion is administered. Non-metabolizable oils suitable for use in compositions of the present invention include alkanes, alkenes, alkynes, and their corresponding acids and alcohols, the ethers and esters thereof, and mixtures thereof. Preferably, the individual compounds of the oil are light hydrocarbon compounds, i.e., such components have 6 to 30 carbon atoms. The oil can be synthetically prepared or purified from petroleum products. Preferred non-metabolizable oils for use in compositions described herein include mineral oil, paraffin oil, and cycloparaffins, for example. The term "mineral oil" refers to a non-metabolizable adjuvant oil that is a mixture of liquid hydrocarbons obtained from petrolatum via a distillation technique. The term is synonymous with "liquefied paraffin", "liquid petrolatum" and "white mineral oil." The term is also intended to include "light mineral oil," i.e., oil which is similarly obtained by distillation of petrolatum, but which has a slightly lower specific gravity than white mineral oil. Mineral oil can be obtained from various commercial sources, for example, J. T. Baker (Phillipsburg, Pa.), USB Corporation (Cleveland, Ohio). Light mineral oil is commercially available under the name DRAKEOL®.

Adjuvants include, but are not limited to, the Emulsigen adjuvant system (MVP Laboratories; Ralston, Nebr.), the RIBI adjuvant system (Ribi Inc.; Hamilton, Mont.), alum, aluminum hydroxide gel, oil-in water emulsions, water-in-oil emulsions such as, e.g., Freund's complete and incomplete adjuvants, Block copolymer (CytRx; Atlanta, Ga.), SAF-M (Chiron; Emeryville, Calif.), AMPHIGEN® adjuvant, saponin, Quil A, QS-21 (Cambridge Biotech Inc.; Cambridge, Mass.), GPI-0100 (Galenica Pharmaceuticals, Inc.; Birmingham, Ala.) or other saponin fractions, monophosphoryl lipid A, Avridine lipid-amine adjuvant, heat-labile enterotoxin from *E. coli* (recombinant or otherwise), cholera toxin, muramyl dipeptide, squalene/pluronic block copolymer/surfactant (SP-oil), sulpholipobeta-cyclodextrin (SL-CD), liposomes containing an immumodulator (e.g., CpG or poly I:C), muramyl dipeptide (MDP), iscomatrix (Quil A/phosphotidyl choline), CpG/DEAE-dextran/mineral oil (TXO), CpG, triterpenoids (e.g., Quil A or another purified or partially purified saponin preparation), sterols (e.g., cholesterol), immunomodulatory agents (e.g., dimethyl dioctadecyl ammonium bromide—DDA), polymers (e.g., polyacrylic acid such as CARBOPOL®), and Th2 stimulants (e.g., glycolipids such as Bay R1005®), and combinations thereof, among many other adjuvants known to those skilled in the art.

Non-limiting examples of various combinations that can be used include a triterpenoid plus a sterol (e.g., Quil A/cholesterol, also known as QAC), a triterpenoid plus a sterol, an immunomodulatory agent, and a polymer (e.g., Quil A/cholesterol/DDA/CARBOPOL®, also known as QCDC), and a triterpenoid plus a sterol, an immunomodulatory agent, a polymer, and a Th2 stimulant (e.g., Quil A/cholesterol/DDA/CARBOPOL®, and Bay R1005®, also known as QCDCR).

The amounts and concentrations of adjuvants and additives useful in the context of the present invention can readily be determined by the skilled artisan. In one embodiment, the present invention contemplates immunogenic compositions and vaccines comprising from about 20 μg to about 2000 μg of adjuvant. In another embodiment, adjuvant is included in an amount from about 100 μg to about 1500 μg, or from about 250 μg to about 1000 μg, or from about 350 μg to about 750 μg. In another embodiment, adjuvant is included in an amount of about 500 μg/2 ml dose of the immunogenic composition or vaccine.

The immunogenic compositions and vaccines can also include antibiotics. Such antibiotics include, but are not limited to, those from the classes of aminoglycosides, carbapenems, cephalosporins, glycopeptides, macrolides, penicillins, polypeptides, quinolones, sulfonamides, and tetracyclines. In one embodiment, the present invention contemplates immunogenic compositions and vaccines comprising from about 1 μg/ml to about 60 μg/ml of antibiotic. In another embodiment, the immunogenic compositions and vaccines comprise from about 5 μg/ml to about 55 μg/ml of antibiotic, or from about 10 μg/ml to about 50 μg/ml of antibiotic, or from about 15 μg/ml to about 45 μg/ml of antibiotic, or from about 20 μg/ml to about 40 μg/ml of antibiotic, or from about 25 μg/ml to about 35 μg/ml of antibiotic. In yet another embodiment, the immunogenic compositions and vaccines comprise less than about 30 μg/ml of antibiotic.

Immunogenic compositions and vaccines encompassed by the present invention can include one or more polynucleotide molecules encoding for a virus or bacteria, or viral or bacterial protein. DNA or RNA molecules can be used in immunogenic compositions or vaccines. The DNA or RNA molecule can be administered absent other agents, or it can be administered together with an agent facilitating cellular uptake (e.g., liposomes or cationic lipids). Total polynucleotide in the immunogenic composition or vaccine will generally be between about 0.1 μg/ml and about 5.0 mg/ml. In another embodiment, the total polynucleotide in the immunogenic composition or vaccine will be from about 1 μg/ml and about 4.0 mg/ml, or from about 10 μg/ml and about 3.0 mg/ml, or from about 100 μg/ml and about 2.0 mg/ml. Vaccines and vaccination procedures that utilize nucleic acids (DNA or mRNA) have been well described in the art, for example, U.S. Pat. Nos. 5,703,055, 5,580,859, 5,589,466, all of which are incorporated herein by reference.

In addition to the viruses or bacteria described above, immunogenic compositions and vaccines encompassed by the present invention can include other additional antigens. Antigens can be in the form of an inactivated whole or partial preparation of the microorganism, or in the form of antigenic molecules obtained by genetic engineering techniques or chemical synthesis. Other antigens appropriate for use in accordance with the present invention include, but are not limited to, those derived from pathogenic viruses such as IPNV.

Administration

In a preferred embodiment of the invention, fish are vaccinated with an amount of a recombinant antigen that is effective to provide protection against disease caused by the same species as the pathogen from which the antigen was derived, wherein immersion of the fish in water containing the antigen produces an immune response in the fish, preferably providing protection against the pathogen Skin epithelium and gills of fish have mechanisms to protect fish in a broad as well as specific way, effectively allowing them to recognize pathogens they have been in contact with. When fish are immersed in water containing a diluted vaccine, the suspended antigens from the vaccine may be adsorbed by the skin and gills. Then specialized cells, such as antibody-secreting cells, present in the skin and gill epithelium, will be activated and protect the fish when exposed to the live pathogen at a later stage. Other cells located in the epithelium of skin and gills, such as antigen presenting cells (macrophages), also absorb vaccine antigens and transport them to specialised tissues where the systemic immune response builds up.

In immersion vaccination, there are several application methods including dip and bath. In dip vaccination, fish are immersed for a very short duration, usually 30 seconds, in a highly concentrated vaccine solution, usually 1 part vaccine product to 9 parts water. With bath vaccination, fish are exposed for a longer period, usually one to several hours, in a lower concentration of vaccine. The present invention contemplates both dip and bath methodologies for the immersion vaccines. Additionally, the fish can be exposed to the vaccine composition through spray techniques known to those of skill in the art.

Techniques for use and administration of immersion vaccines are disclosed in the following patents, the contents of which are incorporated by reference as if set forth fully herein. U.S. Pat. No. 6,518,252 relates to an immersion and bath method to reduce the infection load of an aquatic animal. U.S. Pat. No. 6,893,667 relates to a method to deliver a preparation of powdered nucleic acid molecules into vertebrate tissue for transformation of cells in the tissue using needleless injection techniques. U.S. Pat. No. 6,872,386 relates to an oral vaccine that includes a multiple-cell organism for use as food for an aquatic animal to be vaccinated, and a single-cell organism fed to, and as a result, bioencapsulated by, the multiple-cell organism. U.S. Pat. No. 6,855,372 relates to a method and apparatus for coating skin-piercing microprojections. U.S. Pat. No. 6,673,374 relates to an anti-microbial composition for the treatment of human skin affected by dermatitis of different etiologies, made from hydrogen peroxide, one or more moisturizing agents and an anti-inflammatory agent; and optionally including an exfoliating agent; the compositions therein can be incorporated into the immersion vaccines described herein. U.S. Pat. No. 6,699,907 relates to a composition of anti-microbial action made from a polar lipophilic solvent and fatty acids with 8 to 14 carbons. U.S. Pat. No. 4,009,259 relates to a method for treating fish and increasing the efficiency of vaccines or disinfectants, wherein the fish are submerged in hyperosmotic solutions for 2 to 3 minutes, and are then submerged in another solution of the immersion vaccine or chemotherapeutic solutions. These solutions are made from sodium, potassium, calcium and magnesium salts under the form of sulfates, chlorides or phosphates. U.S. Pat. No. 4,282,828 relates to an apparatus to apply immersion vaccines by the direct aspersion of the vaccine in a spray. The fish are confined in a rectangular receptacle where they are exposed to such a bathing procedure. U.S. Pat. No. 4,287,179 relates to a procedure to apply an immersion vaccine for the red mouth disease (yersiniosis) by simply applying the vaccine in the form of a non-pressurized immersion. U.S. Pat. No. 4,363,290 relates to an automatic apparatus to apply one or more immersion vaccines, which consists of a means to lead the fish into a compartment containing the vaccinal solution and later, once the required immersion contact time is completed, divert the fish toward their outside habitat.

The water in which the fish are immersed may be freshwater, saltwater, or brackish, depending on the variety of fish to be treated and the natural habitat of the fish. The amount of antigen that is delivered to the fish is an amount that is effective to provide protection against disease caused by the pathogen. For example, the amount of antigen in the water in which the fish are immersed is effective to provide protection. The fish are immersed in the water, or sprayed with a fluid, containing the antigen for a time that is sufficient for the development of protection against disease caused by the wild-type pathogen. Generally, immersion times between 15 seconds and several hours are suitable for the method of the invention. Preferably, the immersion time is between 1 minute and two hours. More preferably, immersion time is between 15 minutes and 2 hours. A most preferred immersion time is between 30 minutes and 1 hour.

For purposes of this invention, protection against disease due to the method of the invention is considered to have been elicited when complete or partial immunity against the disease has been obtained. Immunity is considered as having been obtained in a population of treated fish when the level of protection for the population, evidenced by a decrease in the number of infected fish or in severity of disease, is higher in fish that have been treated in accordance with the invention than that of an unvaccinated control group. Preferably, vaccination in accordance with the method of the invention will result in a decrease of 20% in mortality due to the disease or in the number of individuals showing clinical signs of the disease compared to unvaccinated controls.

Immunogenic compositions and vaccines of the present invention include a therapeutically effective amount of one or more of the above-described microorganisms. Purified viruses and/or bacteria can be used directly in an immunogenic composition or vaccine, or can be further attenuated, or inactivated. Typically, an immunogenic composition or vaccine contains between about 1×10² and about 1×10¹² viral or bacterial particles, or between about 1×10³ and about 1×10¹¹ particles, or between about 1×10⁴ and about 1×10¹⁰ particles, or between about 1×10⁵ and about 1×10⁹ particles, or between about 1×10⁶ and about 1×10⁸ particles. The precise amount of a microorganism in an immunogenic composition or vaccine effective to provide a protective effect can be determined by a skilled artisan.

In accordance with the methods of the present invention, a single dose can be administered to animals, or, alternatively, two or more inoculations can take place with intervals of from about two to about ten weeks. Boosting regimens can be required, and the dosage regimen can be adjusted to provide optimal immunization. Those skilled in the art can readily determine the optimal administration regimen.

The solubility of materials used in the preparation of parenteral solutions can be increased by the use of appropriate formulation techniques known to the skilled artisan, such as the incorporation of solubility-enhancing agents, including buffers, salts, surfactants, liposomes, cyclodextrins, and the like.

The extent and nature of the immune responses induced in the animal can be assessed by using a variety of techniques. For example, sera can be collected from the inoculated animals, and tested for the presence or absence of antibodies specific for the immunogens. Detection of responding cytotoxic T-lymphocytes (CTLs) in lymphoid tissues, indicative of the induction of a cellular immune response, can be achieved by assays such as T cell proliferation. The relevant techniques are well described in the art.

Kits

Inasmuch as it may be desirable to administer an immunogenic composition or vaccine in combination with additional compositions or compounds—for example, for the purpose of treating a particular disease or condition—it is within the scope of the present invention that an immunogenic composition or vaccine can conveniently be included in, or combined in, the form of a kit suitable for administration or co-administration of the compositions.

Thus, kits encompassed by the present invention can comprise one or more separate pharmaceutical compositions, at least one of which is an immunogenic composition or vaccine in accordance with the present invention, and a means for separately retaining said compositions, such as a container, divided bottle, or divided foil packet. An example of such a kit is a syringe and needle, and the like. A kit of the present invention is particularly suitable for administering different dosage forms, for example, oral or parenteral, for administering the separate compositions at different dosage intervals, or for titrating the separate compositions against one another. To assist one administering a composition encompassed by the present invention, the kit typically comprises directions for administration.

Another kit encompassed by the present invention can comprise one or more reagents useful for the detection of an infected animal. The kit can include reagents for analyzing a sample for the presence of whole microorganisms, polypeptides, epitopes or polynucleotide sequences. The presence of virus, bacteria, polypeptides, or polynucleotide sequences can be determined using antibodies, PCR, hybridization, and other detection methods known to those of skill in the art.

Another kit encompassed by the present invention can provide reagents for the detection of antibodies against particular epitopes. Such reagents are useful for analyzing a sample for the presence of antibodies, and are readily known and available to one of ordinary skill in the art. The presence of antibodies can be determined using standard detection methods known to those of skill in the art.

In certain embodiments, the kits can include a set of printed instructions, or a label indicating that the kit is useful for the detection of infected animals.

General Cloning Strategies and Vaccine/Antigen Constructions

*F. psychrophilum* Antigen CM8 (SEQ ID NO: 7)

The donor gene was a 276 bp gene sequence (Fp91), encoding an 86 aa truncated form of the 91 aa histone-like DNA binding protein (termed 8) from *F. psychrophilum* (GenBank™ Accession #AAR29587).

Upstream of the histone-like protein gene is a leader sequence, termed C. Sequence C encodes a 90 amino acid fragment of the cellulose-binding protein precursor of *Clostridium cellulovorans*; the cellulose-binding protein precursor from which C was derived consists of 1848 amino acids (GenBank™ Accession #P38038). Sequence C is followed by an additional 6 amino acids derived from a DNA sequence containing Bam HI and Nde I restriction sites with a short spacer between them. The 90 amino acid peptide fragment C is used to facilitate high-level expression and ensure insolubility of the target protein as inclusion bodies in *E. coli*.

Immediately following the leader sequence C is fragment M, which encodes a 15 amino acid immunostimulatory peptide from the measles virus fusion peptide (MVF) (GenBank™ M81903) (L SEIKGVIVHRLEG V). The M DNA segment (representing a T cell epitope) was optimized for high-level expression in *E. coli* (Kuzyk, Burian et al. 2001).

None of the DNA fragments carried any regulatory elements. Transcriptional and translational signals specific for *E. coli* were provided by the expression plasmid(s).

The expression cassette consists of a ribosome binding site sequence, a peptide C leader sequence, T-cell epitope "M" and the *F. psychrophilum* gene (Fp91) encoding protein antigen "8" and was constructed as follows:

The N-terminal fusion peptide was fused to the donor gene in an effort to facilitate high expression levels in *E. coli*. The fragment "C", encoding the leader peptide C and a ribosome binding site (RBS), was cloned between XbaI and Bam HI sites of pET21a(+) (Novagen) resulting in plasmid pETC. The relevant fragment "C" was synthesized using four overlapping oligonucleotides and the PCR technique. The result of the PCR reaction was a DNA fragment 5'-Xba I-RBS-C-Hind III-3'.

The target antigen gene from *F. psychrophilum* was identified as a histone-like protein. The PCR technique was used to create the *F. psychrophilum* gene of interest with flanking restriction enzyme sites. PCR amplified DNA was cloned into plasmid pBCKS-V as BamHI-HindIII fragments resulting in pBCKS-V-8. Fragment 8 was then cloned from pBCKS-V-8 as a Bam HI-Ase I fragment into plasmid pETC digested with Bam HI and Nde I, resulting in pETC8.

The measles virus epitope (M) was cloned into pETC8 between peptide C and the *F. psychrophilum* gene "8" as follows: The M coding region was removed from pBCKS-V-M by digestion with Bam HI and Ase I and subcloned into the Bam HI and Nde I site of pETC8, resulting in pETCM8 (Ase I and Nde I produce compatible cohesive DNA ends, which can be ligated by DNA ligase). Plasmid pETCM8 is a T7 expression vector based on pET21a(+).

Expression of the recombinant protein cassette CM8 was verified upon induction of the T7 promoter.

The resulting protein was designated as "*F. psychrophilum* rHLP" or "rHLP" antigen that was used in the Examples below and is described in SEQ ID NO: 7.

IPNV Construct

The genome segment A of IPNV contains three genes arranged in the order 5'-VP2-NS-VP3-3'. VP2 encodes the IPNV surface glycoprotein. Segment designed VP2', consisting of 1-257 amino acids of VP2 was selected for a vaccine development.

The VP2c DNA sequence including and selected T-cell epitopes sequences was synthesized using method of overlapping oligonucleotides and verified by DNA sequencing methods.

Antigen Cassette VP2c:

The DNA sequence encloding rIPNV antigen cassette designed "VP2c" was designed as follows: DNA sequence containing Barn HI and Nde I restriction sites followed by VP2c fragment encoding 1-257 amino acid of viral VP2 protein plus amino acid sequence "KKKAKKKQL" (SEQ ID NO: 11); and finally DNA sequence containing Vsp I and Hind III restriction sites.

Expression Cassette CTMVP2c in Production Plasmid pKLPR-CTMVP2c:

The DNA sequence encoding the target recombinant protein CTMVP2c was designed as follows: the leader sequence C encodes 90 amino acids derived from the cellulose-binding protein A precursor of *Clostridium cellulovorans* (GenBank™ Accession #P38038); it is followed by an additional 6 amino acids derived from a DNA sequence containing Barn HI and Nde I restriction sites; this is followed with DNA sequence encoding the promiscuous T cell epitope from *Clostridium tetani* tetanus toxin (tt) P2 epitope (830-844)(GenBank™ AA037454) designed "T" (QYIKANSKFIGITEL) (SEQ ID NO: 12); followed with the promiscuous T cell epitope from measles virus (288-302)(GenBank™ M81903); designated "M" (LSEIKGVIVHRLEGV) (SEQ ID NO: 10); this is followed with DNA sequence encoding VP2c and finally DNA sequence containing Vsp 1 and Hind III restriction sites.

The *Escherichia coli* BL21 recipient organism contained a single plasmid, pKLPR-CTMVP2c, which contained the expression cassette CTMVP2c expressing the IPNV vaccine recombinant protein. This expression cassette consists of a ribosome binding site sequence, a protein C leader sequence, IPNV antigen VP2c sequence preceded with immunostimulatory sequences from measles virus fusion protein and tetanus toxin. The details of the construction are described below.

Antigen cassette VP2c was synthesized by TOP Gene Technologies, Quebec, Canada based on DNA sequence designed by Microtek Research and Development Ltd. Relevant sequence is a consensus sequence of a fragment of gene VP2 from several recent IPNV SP serotype isolates from Chile and Norway. Synthetic DNA sequence delivered was cloned as Bam HI-Hind III fragment into plasmid pBCKS-V (plasmid used to carry cloning/expression cassettes) for next construction steps resulting in plasmid pBCKS-VP2c.

In order to create an expression cassette VP2c was moved from pBCKS-VP2c to pETC as Bam HI-Hind III fragment resulting to plasmid pETC-VP2c. Cassettes carrying M and T promiscuous T-cell epitopes, excised from pBCKS-V-M and pBCKS-V-T as Bam HI-Vsp I fragments, were subsequently sequentially inserted into pET-VP2c digested with Bain HI and Nde I resulting plasmid pETC-MVP2c and finally plasmid pETC-TMVP2c.

In the final construction step, the DNA expression cassette encoding the CTMVP2c fusion protein with the appropriate ribosome binding site was excised from pETC-TMVP2c as an Xba I—Xho I restriction fragment and cloned into the Xba I and Sal I sites of production expression plasmid pKLPR-8 (proprietary plasmid expression vector of Microtek R&D Ltd.) resulting in the final production plasmid pKLPR-CTMVP2c.

As in SEQ ID NO: 8 The CTMVP2c expression cassette expressed an amino acid sequence consisting of the N-terminal Protein C, the immunostimulatory Measles Virus Fusion protein epitope, the Tetanus toxin protein epitope, the VP2 sequence as described above.

The resulting protein was designated as "IPNV rVP2" antigen that was used in the Examples below and is described in SEQ ID NO: 8.

The fusion protein between the rVP2 and rHLP immunogenic compositions was constructed and expressed using materials and methods similar to those used in the individual immersion vaccine constructs and recovered as inclusion bodies from *E. coli*. The fusion protein sequence as used in the present Examples is shown in SEQ ID NO: 9.

The present invention is further illustrated by, but by no means limited to, the following examples.

EXAMPLES

Example 1

Immersion Vaccination of Atlantic Salmon (*Salmo salar*) Fry with Monovalent IPNV (IPNV rVP2) and Bivalent *Flavobacterium psychrophilum* (rHLP Vaccine Antigen)-IPNV VP2 Vaccine Antigen Vaccines The main objective of this study was to determine whether a monovalent IPNV vaccine, and a bivalent *F. psychrophilum* histone-like protein (HLP): IPNV VP2 vaccine, when administered by immersion to Atlantic salmon fry, could induce significant protection against a lethal challenge of IPNV. In this study, 2 doses of a monovalent IPNV immersion vaccine were tested. In addition, two types of bivalent formulations were also evaluated, to investigate whether the inclusion of a *F. psychrophilum* vaccine component would interfere with protection against IPNV. The fish were purchased from Australis S. A. Farmed (Peñaflor, Chile), tested to be pathogen free prior to use, and had a mean weight of approximately 0.5 g at the time of challenge. Fish were housed in 21 L tanks until random selection for vaccination. After 1 week acclimation, all fish were transferred into 1 L flasks, and vaccinated with the vaccines as described in Table 1, for 2 minutes. Vaccinates were then returned to 21 L tanks until challenge. Challenge occurred at 400 degree days (A "degree day"=° C.×number of days in holding; 400 degree days=12° C.×~34 days), and was carried out by immersion in 9 L tank for 2 hours. The challenge strain was IPNV strain Sp, recently isolated from Chile; $10^5$ pfu/ml IPNV was used. Control groups were subjected to the same conditions as the vaccinates (i.e. vaccination in 1 L flasks for 2 min; challenge in 9 L tanks for 2 hrs). After challenge, fish were returned to 21 L tanks, where the water temperature was kept at 12±2° C. Fish were offered up to 1% body weight daily manually of the appropriate fish feed. Vaccines (Table 1) were prepared as follows:

1) Recombinant *F. psychrophilum* histone-like protein (rHLP) was expressed as insoluble inclusion bodies in *Escherichia coli* BL21 cells, which were then passed through a microfluidiser, and the insoluble protein partially purified by centrifugation. The protein suspension was stored 4-6° C. in 0.5 mM EDTA. The concentration of HLP in the inclusion body suspension was calculated (by SDS PAGE, scanning densitometry and comparison to BSA standards) to be 1.76 µg/µl.

2) Acid-treated recombinant *F. psychrophilum* rHLP was expressed as insoluble inclusion bodies, in 3 separate fermentor runs. The final, washed inclusion body suspension was pH-treated with concentrated HCl, followed by 10 N NaOH, to bring the pH back to 7. The cells were lysed with thymol/EDTA, and passed through a microfluidiser. To concentrate the insoluble inclusion body preparation and remove thymol, the protein suspension was filtered, and 10 volumes of sterile water were passed through the filtration unit. The concentration of HLP in the inclusion body suspension was calculated to be 0.72 µg/µl.

3) A recombinant fusion protein, consisting of *F. psychrophilum* HLP fused to IPNV VP2, was expressed as insoluble inclusion bodies in *E. coli* BL21 cells. The cells were lysed with thymol/EDTA, and passed through a microfluidiser. The insoluble protein was partially purified by centrifugation, and resuspended in thymol/EDTA solution. The inclusion body preparation was then washed six times by centrifugation to remove thymol, resuspended in sterile 0.05 mM EDTA, and stored at 4-6° C. The concentration of the fusion protein was calculated to be 10.02 μg/μl.

4) Recombinant IPNV VP2 was expressed as insoluble inclusion bodies in *E. coli* BL21 cells. The cells were lysed with thymol/EDTA, and passed through a microfluidiser. The insoluble protein was partially purified by centrifugation, and resuspended in thymol/EDTA solution. The inclusion body preparation was then washed six times by centrifugation to remove thymol, resuspended in sterile 0.05 mM EDTA, and stored at 4-6° C. The concentration of IPNV VP2 protein was calculated to be 10.90 μg/μl.

TABLE 1

Vaccine Formulations.

| Vaccine | Composition |
|---|---|
| A | IPNV rVP2; 100 μg |
| B | IPNV rVP2; 200 μg |
| C | IPNV rVP2; 100 μg + *F. psychrophilum* rHLP; 50 μg |
| D | *F. psychrophilum* rHLP:IPNV rVP2 (fusion protein); 124 μg (molar equivalent to 100 μg rVP2, 50 μg rHLP) (SEQ ID NO: 9) |

For construction of the above described inclusion body vaccine compositions, it will readily be understood by one of skill in the art that certain features can be replaced without departing from the spirit of the invention. For example, alternative leader sequences can be inserted and additional or different T-cell epitopes can be provided with the rHLP and or rVP2 antigens.

Vaccine formulations in Example 1 were administered in concentrations in the same way as described below for Example 2. Following challenge, all groups were monitored for 28 days, at which time there had to be no mortality for 3 consecutive days in all challenge groups. Every mortality was examined externally for disease indications. After external observation, the fish were necropsied and examined internally. Tissue culture confirmation of IPNV infection was performed on a pool of 5 fish from each tank at the end of the study.

On the same day as the challenge, blood was collected and pooled from 20 fish per group, in order to isolate serum. Seroneutralization assays were carried out on the collected sera, in order to evaluate antibody response.

This experiment would have been considered void if either of the following had occurred:

(1) If there was any failure at the testing facility that resulted in significant mortality in either the vaccine groups or the control groups.

(2) If it had been determined that significant deviations to the protocol had occurred.

No such failures occurred.

The percentage mortality was calculated, from those mortalities determined to have occurred as a result of the challenge organism, as follows:

% Mortality={1−(mortality due to challenge)/(total fish challenged)}×100

The relative percent survival (RPS) was calculated at the end of the trial, when the control mortality in the infected fish reached>70%, using the formula described above.

RPS={1−(% vaccinate mortality/% control mortality)}×100

Results.

Eighty-five fish per group were vaccinated with four different vaccines in duplicate: 2 of a monovalent IPNV VP2 vaccine, and 2 of a bivalent *F. psychrophilum* HLP:IPNV VP2 vaccine. No mortality was observed during vaccination. All groups of fish were healthy at the point of challenge. The control groups were observed to be more active and feeding better, compared to the vaccinated groups.

The same day as the challenge, blood was collected and pooled from 20 fish per group, and the serum isolated. Antibody responses, evaluated by seroneutralization assays, showed that the immersion vaccines did not elicit a detectable antibody response in Atlantic salmon fry.

Duplicate groups of 65 fish per vaccine group were challenged with IPNV, with the exception of the negative control groups. Every fish was necropsied. All mortalities per tank were pooled (pools of up to 5) and tested for IPNV. All immersion-challenged groups tested positive for IPNV. The cumulative mortality and relative percent survival (RPS) of each group of fish is shown in Table 2.

TABLE 2

Mortality and RPS in groups of 65 Atlantic salmon fry (0.5 g) challenged with IPNV.

| Vaccine | Cumulative % Mortality | Average % Mortality | % RPS | % Mortality (−) control | % RPS (−) control |
|---|---|---|---|---|---|
| A | 29 | 36 | 53 | 18 | 70 |
| A | 43 | | | | |
| B | 44 | 51 | 34 | 33 | 44 |
| B | 57 | | | | |
| C | 31 | 42 | 45 | 24 | 59 |
| C | 53 | | | | |
| D | 59 | 55 | 29 | 37 | 37 |
| D | 51 | | | | |
| (−) control | (15)* | 18 | 77 | 0 | 100 |
| (−) control | (21)* | | | | |
| (+) control | 74 | 77 | — | 59 | — |
| (+) control | 79 | | | | |

*Mortalities in the infected (−) control grouip tested negative for the presence of IPNV.

Results of IPNV isolation from pools of 5 fish per tank at the end of the trial confirmed that fishes were infected with the virus. The same was observed by necropsies.

The (−) control fish (unvaccinated and unchallenged) reached mortality levels of 15% and 21% by the end of the trial (average=18%). In studies on larger fish, the normal background mortality reaches approximately 5%. Necropsies were performed on all mortalities, and no bacterial or viral infection was confirmed in the (−) control mortalities. Therefore, this background level of mortality is believed to be due to a compilation of stress during handling, and the small size of the fish (0.5 g). Therefore, this background mortality was subtracted from all groups for the purposes of RPS calculations, even though all the other groups tested positive for IPNV.

CONCLUSIONS

Immersion vaccination led to a decrease in mortality in all groups of Atlantic salmon fry. In duplicate groups, Vaccine A (IPNV rVP2) provided the highest level of protection in Atlantic salmon fry, with average RPS of 70%. Vaccine C (IPNV rVP2+F. psychrophilum rHLP) provided the second best results overall, with an average RPS of 59%. The two different dose levels of monovalent vaccine (IPNV rVP2) provided different levels of protection, with the lower dose level (Vaccine A) affording better protection than the higher dose level (Vaccine B). The two different bivalent formulations (Vaccine C; Vaccine D), administered at the same relative dose level, provided different levels of protection, with Vaccine C affording higher levels of protection than Vaccine D.

Example 2

Immersion Vaccination of Rainbow Trout Fry Against *Flavobacterium psychrophilum*

The objectives of this study were to test the efficacy of a recombinant *F. pyschrophilum* histone-like protein (HLP) vaccine (rHLP) at various dosages, as well as different bivalent formulations of a recombinant *F. psychrophilum* HLP (rHLP) and IPNV rVP2 vaccine, all as immersion vaccines in rainbow trout (Oncorhynchus mykiss).

Fish were purchased from Spring Valley Trout Farm (Langley, B.C.), and had mean weights of 0.4 g, 0.6 g and 1.0 g at the time of vaccination. They were housed in one 390 L tank outside for 1 month, until random selection for pre-challenge and vaccination. Vaccines (Table 3) were prepared as follows:

1) Recombinant *F. psychrophilum* histone-like protein (rHLP) was expressed as insoluble inclusion bodies in *Escherichia coli* BL21 cells, which were then passed through a microfluidiser, and the insoluble protein partially purified by centrifugation. The protein suspension was stored 4-6° C. in 0.5 mM EDTA. The concentration of HLP in the inclusion body suspension was calculated (by SDS PAGE, scanning densitometry and comparison to BSA standards) to be 1.76 µg/µl.

2) Acid-treated recombinant *F. psychrophilum* rHLP was expressed as insoluble inclusion bodies, in 3 separate fermentor runs. The final, washed inclusion body suspension was pH-treated with concentrated HCl, followed by 10 N NaOH, to bring the pH back to 7. The cells were lysed with thymol/EDTA, and passed through a microfluidiser. To concentrate the insoluble inclusion body preparation and remove thymol, the protein suspension was filtered, and 10 volumes of sterile water were passed through the filtration unit. The concentration of HLP in the inclusion body suspension was calculated to be 0.72 µg/µl.

3) A recombinant fusion protein, consisting of *F. psychrophilum* HLP fused to IPNV VP2, was expressed as insoluble inclusion bodies in *E. coli* BL21 cells. The cells were lysed with thymol/EDTA, and passed through a microfluidiser. The insoluble protein was partially purified by centrifugation, and resuspended in thymol/EDTA solution. The inclusion body preparation was then washed six times by centrifugation to remove thymol, resuspended in sterile 0.05 mM EDTA, and stored at 4-6° C. The concentration of the fusion protein was calculated to be 10.02 µg/µl.

4) Recombinant IPNV VP2 was expressed as insoluble inclusion bodies in *E. coli* BL21 cells. The cells were lysed with thymol/EDTA, and passed through a microfluidiser. The insoluble protein was partially purified by centrifugation, and resuspended in thymol/EDTA solution. The inclusion body preparation was then washed six times by centrifugation to remove thymol, resuspended in sterile 0.05 mM EDTA, and stored at 4-6° C. The concentration of IPNV VP2 protein was calculated to be 10.90 µg/µl.

TABLE 3

| Vaccine | Description |
|---|---|
| 1 | *F. psychrophilum* rHLP; 50 µg/ml (low dose) |
| 2 | *F. psychrophilum* rHLP; 50 µg/ml (low dose) + 103 µg IPNV rVP2 |
| 3 | *F. psychrophilum* rHLP: IPNV rVP2 (fusion protein); 124 µg/ml (low dose) |
| 4 | *F. psychrophilum* rHLP, acid-treated; 50 µg/ml (low dose) |
| 5 | *F. psychrophilum* rHLP; 200 µg/ml (high dose) |
| 6 | *F. psychrophilum* rHLP; 50 µg/ml (low dose); small fry |
| 7 | *F. psychrophilum* rHLP; 50 µg/ml (low dose); large fry |
| 8 | Untreated control; medium fry |

Fish (120/group) were then transferred into 32.5 L tanks. Fish (30 at a time) were vaccinated by immersion for 2 min in 1 L of de-chlorinated water containing inclusion body recombinant vaccine preparations. Air stones were present during the vaccinations. Concentrations of inclusion body preparations were measured by scanning a SDS-PAGE gel, and comparing it to BSA standards. Fish were returned to the 32.5 L tanks, and remained there until they were challenged. Water temperature was kept constant at 12+1° C., and water flow continuous at 1.0 lpm.

Fish were challenged by immersion after ~408 degree days ("dd"; degree days=° C. multiplied by the number of days in holding); a repeat challenge was performed at ~588 dd. The challenge strain of *F. psychrophilum* (strain C594) was cultivated from frozen stock on agar at 15° C. After 6 days incubation at 15° C., cells were scraped from plates, and resuspended in 15° C. sterile saline. Cells were resuspended to a final $OD_{600}$ 8.4, and maintained at 15° C. Prior to challenge, fish were anaesthetized and transferred to a table, laying them on their right side, head to the left, left side up. Mucus was wiped off the peduncle area using a clean scalpel blade held at a 45°, wiping 3 times from left to right from beneath the adipose fin to the base of the tail. Following this treatment, they were transferred to the 1 L immersion tank. Once all fish per group were in the immersion tank, *F. psychrophilum* was added to a final $OD_{600}$ 0.1. Air was supplied to the tank, and the fish remained in the *F. psychrophilum*-containing suspension for 1 hour, after which time they were then transferred to 14.3 L challenge tanks Fish were monitored for 14 days, until no mortality was observed in all groups for 3 consecutive days. Fish were offered 1% body weight daily (except 24 hours before and after moving, and challenge) with BioClark Fry Feed (Longview, Wash.). Necropsies were performed on approximately 70% of mortalities that occurred. Kidney tissue from mortalities was spread onto agar in order to cultivate the challenge organism. The relative percent survival (RPS) was calculated as follows:

RPS={1−(% vaccinate mortality/% control mortality)}×100

Results.

The vaccination of small fry (0.4 g) resulted in a negative RPS, while vaccination of medium (0.6 g) and large (1.0 g) fry resulted in protection (Table 4). The high dose of monovalent vaccine in medium-sized fry yielded an average of 12% (10% and 13%) mortality, compared to 35% (23% and 47%) mortality in the low dose group. Large fry (1 g at vaccination) appeared to perform very well with the low dose vaccine. However, a large fry control is needed to rule out the effect of size on challenge. Medium-sized fish were used to calculate RPS, as this was the size of the only control group.

Discussion.

The large fry received only the low dose vaccine, but appeared to perform the best overall. Two possible explanations are that: (1) Fish vaccinated at 1 g are able to mount a more effective immune response that fish vaccinated at 0.6 g, and therefore respond much better to the low dose vaccine; or (2) The larger fry fare better during challenge compared to the medium-sized controls. At the time of challenge, the large fry were much closer in size to the medium sized naive controls (2.3 g vs 2.1 g at 588 dd, 10% bigger; 1.9 g vs 1.6 g at 408 dd, 19% bigger) than they were at the time of vaccination (1 g vs 0.6 g, 67% bigger). Medium-sized fish were vaccinated with either the low dose (50 ug/ml) or high dose (200 ug/ml) rHLP vaccine. When challenged at 408 dd, the high dose groups performed much better, with RPS values of 77% and 69%, compared to 46% and −8%.

No negative interference was observed when a second antigen (IPNV rVP2) was mixed with the *Flavobacterium* rHLP antigen. In fact, the mixture, which contained more protein overall but the same dose of rHLP, appeared to provide greater protection than the monovalent rHLP alone, with RPS values of 69% and 46% for the mixture, compared to 46% and 53% RPS for the monovalent at 408 dd. The results for the fusion protein were inconsistent, however, with RPS values of 62% and 8% at 408 dd.

TABLE 4

Effect of Vaccination on % Mortality and RPS.

| | | 408 dd Challenge* | | | 538 dd Challenge | | |
|---|---|---|---|---|---|---|---|
| Vaccine | Vaccination Size (g) | Challenge Size (g) | % Mortality | RPS | Challenge Size (g) | % Mortality | RPS |
| (pre-challenge) | — | 1.7 | 50 | — | | | |
| 8 | 0.6 | 1.6 | 50 | — | 2.1 | 16 | — |
| 8 | 0.6 | 1.6 | 37 | — | 2.1 | 28 | — |
| 7 | 1 | 1.9 | 3 | 92 | 2.3 | 4 | 82 |
| 7 | 1 | 1.9 | 0 | 100 | 2.3 | 4 | 82 |
| 1 | 0.6 | 1.6 | 23 | 46 | 1.8 | 32 | −45 |
| 1 | 0.6 | 1.6 | 47 | 53 | 1.8 | 16 | 27 |
| 6 | 0.4 | 1.2 | 60 | −38 | 1.5 | 68 | −209 |
| 6 | 0.4 | 1.2 | 63 | −46 | 1.5 | 64 | −191 |
| 4 | 0.6 | 1.6 | 7 | 85 | 1.9 | 32 | −45 |
| 4 | 0.6 | 1.6 | 33 | 23 | 1.9 | 8 | 64 |
| 5 | 0.6 | 1.6 | 10 | 77 | 2.0 | 0 | 100 |
| 5 | 0.6 | 1.6 | 13 | 69 | 2.0 | 16 | 27 |
| 2 | 0.6 | 1.6 | 13 | 69 | 1.8 | 12 | 45 |
| 2 | 0.6 | 1.6 | 23 | 46 | 1.8 | 24 | −9 |
| 3 | 0.6 | 1.6 | 17 | 62 | 1.7 | 48 | −118 |
| 3 | 0.6 | 1.6 | 40 | 8 | 1.7 | 24 | −9 |

*Challenge size at 408 dd measured from leftover fry in same group 4 days post-challenge

The invention claimed is:

1. An immersion vaccine for fish comprising at least one isolated antigen having the amino acid sequence of SEQ ID NO: 7.

2. The immersion vaccine of claim 1, wherein the vaccine further comprises at least a second different isolated antigen.

3. The immersion vaccine of claim 2, wherein the second isolated antigen is an infectious pancreatic necrosis virus (IPNV) antigen.

4. The immersion vaccine of claim 1, further comprising at least one additional agent selected from the group consisting of *Aeromonas hydrophilia, Aeromonas salmonicida, Pseudomonas fluorescens, Vibrio anguillarum, Vibrio salmonicida, Renibacterium salmoninarum*, infectious haemopoietic necrosis virus (IHNV), infectious salmon anemia virus (ISAV), pancreas disease virus (PDV), salmon alphavirus (SAV), salmon poxvirus, and viral haemorrhagic septicemia virus (VHSV).

5. A method of immunizing a fish against *Flavobacterium psychrophilum* comprising administering to said fish an immunologically effective amount of the immersion vaccine of claim 1.

6. An immersion vaccine for fish comprising at least one of: (a) the amino acid sequence of SEQ ID NO: 9; or (b) the amino acid sequence of SEQ ID NO: 7 and SEQ ID NO: 8.

* * * * *

SEQUENCE LISTING

<160> NUMBER OF SEQ ID NOS: 12

<210> SEQ ID NO 1
<211> LENGTH: 270
<212> TYPE: DNA
<213> ORGANISM: Flavobacterium sp.

<400> SEQUENCE: 1

```
atgaacaaat cagatttaat cgatgcaatg gctgctgatg caggaatttc aaaggctgct      60
gctaaagctg ctttagactc tttaacgaat aatattaccg ctactttaaa gaaaggtgat     120
aaagttgctt tagttggatg gggaacttgg tctgtatcac aaagagctgc taggactggt     180
agaaatccac aaacaggagc cgaaattaat attgctgcta aaaatgtagt taagtttaaa     240
gctggagctg gattaagtga tgctgtaaac                                      270
```

<210> SEQ ID NO 2
<211> LENGTH: 90
<212> TYPE: PRT
<213> ORGANISM: Flavobacterium sp.

<400> SEQUENCE: 2

```
Met Asn Lys Ser Asp Leu Ile Asp Ala Met Ala Ala Asp Ala Gly Ile
1               5                   10                  15

Ser Lys Ala Ala Ala Lys Ala Ala Leu Asp Ser Leu Thr Asn Asn Ile
            20                  25                  30

Thr Ala Thr Leu Lys Lys Gly Asp Lys Val Ala Leu Val Gly Trp Gly
        35                  40                  45
```

Thr Trp Ser Val Ser Gln Arg Ala Ala Arg Thr Gly Arg Asn Pro Gln
        50                  55                  60

Thr Gly Ala Glu Ile Asn Ile Ala Ala Lys Asn Val Val Lys Phe Lys
65                  70                  75                  80

Ala Gly Ala Gly Leu Ser Asp Ala Val Asn
                85                  90

<210> SEQ ID NO 3
<211> LENGTH: 273
<212> TYPE: DNA
<213> ORGANISM: Flavobacterium sp.

<400> SEQUENCE: 3
atgaacaaat cagatttaat cgatgctatg gctgctgatg caggaattac taaagctgct     60
gcaaaggctg cattagagtc atttttaagt aatgttgaag aactttaagt aaaggtggt    120 aaagttgctt tagtaggatt cggatcatgg tcagtatcta caagagcggc tagagaagga   180
agaaatcccc aaacagggaa cactattaaa attgaagcta aaacgtagt aaaatttaaa    240 gcaggtgctg aattagaaat agcagtaaat aaa                                 273

<210> SEQ ID NO 4
<211> LENGTH: 91
<212> TYPE: PRT
<213> ORGANISM: Flavobacterium sp.

<400> SEQUENCE: 4

Met Asn Lys Ser Asp Leu Ile Asp Ala Met Ala Ala Asp Ala Gly Ile
1               5                   10                  15

Thr Lys Ala Ala Ala Lys Ala Ala Leu Glu Ser Phe Leu Ser Asn Val
                20                  25                  30

Glu Gly Thr Leu Ser Lys Gly Gly Lys Val Ala Leu Val Gly Phe Gly
            35                  40                  45

Ser Trp Ser Val Ser Thr Arg Ala Ala Arg Glu Gly Arg Asn Pro Gln
        50                  55                  60

Thr Gly Asn Thr Ile Lys Ile Glu Ala Lys Asn Val Val Lys Phe Lys
65                  70                  75                  80

Ala Gly Ala Glu Leu Glu Ile Ala Val Asn Lys
                85                  90

<210> SEQ ID NO 5
<211> LENGTH: 258
<212> TYPE: DNA
<213> ORGANISM: Flavobacterium sp.

<400> SEQUENCE: 5
atgaacaaat cagatttaat cgatgcaatg tcagcttcag ctggaattac aaaagctgct     60
gccaaattag ccttagaatc attttaggc aatattgaag aaactttgca aaaggtgga    120 agagtttctc tagttggatt tggatcttgg tctgtatcta acagagctgc aagagacgga   180
agaaacccac aaacaggagc aacaattaaa attgctgcta aaacgtagt gaaatttaaa    240 gcaggtgctg aattagaa                                                 258

<210> SEQ ID NO 6
<211> LENGTH: 86
<212> TYPE: PRT
<213> ORGANISM: Flavobacterium sp.

<400> SEQUENCE: 6

```
Met Asn Lys Ser Asp Leu Ile Asp Ala Met Ser Ala Ser Ala Gly Ile
1               5                   10                  15

Thr Lys Ala Ala Ala Lys Leu Ala Leu Glu Ser Phe Leu Gly Asn Ile
            20                  25                  30

Glu Glu Thr Leu Gln Lys Gly Gly Arg Val Ser Leu Val Gly Phe Gly
            35                  40                  45

Ser Trp Ser Val Ser Asn Arg Ala Ala Arg Asp Gly Arg Asn Pro Gln
50                      55                  60

Thr Gly Ala Thr Ile Lys Ile Ala Ala Lys Asn Val Val Lys Phe Lys
65                  70                  75                  80

Ala Gly Ala Glu Leu Glu
            85

<210> SEQ ID NO 7
<211> LENGTH: 198
<212> TYPE: PRT
<213> ORGANISM: Flavobacterium psychrophilum

<400> SEQUENCE: 7

Met Ser Val Glu Phe Tyr Asn Ser Asn Lys Ser Ala Gln Thr Asn Ser
1               5                   10                  15

Ile Thr Pro Ile Ile Lys Ile Thr Asn Thr Ser Asp Ser Asp Leu Asn
            20                  25                  30

Leu Asn Asp Val Lys Val Arg Tyr Tyr Tyr Thr Ser Asp Gly Thr Gln
            35                  40                  45

Gly Gln Thr Phe Trp Cys Asp His Ala Gly Ala Leu Leu Gly Asn Ser
50                      55                  60

Tyr Val Asp Asn Thr Ser Lys Val Thr Ala Asn Phe Val Lys Glu Thr
65                  70                  75                  80

Ala Ser Pro Thr Ser Thr Tyr Asp Thr Tyr Leu Asp Pro Ser His Met
            85                  90                  95

Leu Ser Glu Ile Lys Gly Val Ile Val His Arg Leu Glu Gly Val Ile
            100                 105                 110

Met Asn Lys Ser Asp Leu Ile Asp Ala Met Ser Ala Ser Ala Gly Ile
            115                 120                 125

Thr Lys Ala Ala Ala Lys Leu Ala Leu Glu Ser Phe Leu Gly Asn Ile
            130                 135                 140

Glu Glu Thr Leu Gln Lys Gly Gly Arg Val Ser Leu Val Gly Phe Gly
145                 150                 155                 160

Ser Trp Ser Val Ser Asn Arg Ala Ala Arg Asp Gly Arg Asn Pro Gln
                165                 170                 175

Thr Gly Ala Thr Ile Lys Ile Ala Ala Lys Asn Val Val Lys Phe Lys
            180                 185                 190

Ala Gly Ala Glu Leu Glu
            195

<210> SEQ ID NO 8
<211> LENGTH: 397
<212> TYPE: PRT
<213> ORGANISM: Artificial sequence
<220> FEATURE:
<223> OTHER INFORMATION: Synthetic

<400> SEQUENCE: 8

Met Ser Val Glu Phe Tyr Asn Ser Asn Lys Ser Ala Gln Thr Asn Ser
1               5                   10                  15

Ile Thr Pro Ile Ile Lys Ile Thr Asn Thr Ser Asp Ser Asp Leu Asn
```

```
            20                  25                  30
Leu Asn Asp Val Lys Val Arg Tyr Tyr Thr Ser Asp Gly Thr Gln
            35                  40                  45

Gly Gln Thr Phe Trp Cys Asp His Ala Gly Ala Leu Leu Gly Asn Ser
 50                  55                  60

Tyr Val Asp Asn Thr Ser Lys Val Thr Ala Asn Phe Val Lys Glu Thr
 65                  70                  75                  80

Ala Ser Pro Thr Ser Thr Tyr Asp Thr Tyr Leu Asp Pro Ser His Met
                85                  90                  95

Gln Tyr Ile Lys Ala Asn Ser Lys Phe Ile Gly Ile Thr Glu Leu Ile
                100                 105                 110

Met Leu Ser Glu Ile Lys Gly Val Ile Val His Arg Leu Glu Gly Val
                115                 120                 125

Ile Met Asn Thr Asn Lys Ala Thr Ala Thr Tyr Leu Lys Ser Ile Met
                130                 135                 140

Leu Pro Glu Thr Gly Pro Ala Ser Ile Pro Asp Asp Ile Thr Glu Arg
145                 150                 155                 160

His Ile Leu Lys Gln Glu Thr Ser Ser Tyr Asn Leu Glu Val Ser Glu
                165                 170                 175

Ser Gly Ser Gly Ile Leu Val Ser Phe Pro Gly Ala Pro Gly Ser Arg
                180                 185                 190

Ile Gly Ala His Tyr Arg Trp Asn Ala Asn Gln Thr Gly Leu Glu Phe
                195                 200                 205

Asp Gln Trp Leu Glu Thr Ser Gln Asp Leu Lys Lys Ala Phe Asn Tyr
                210                 215                 220

Gly Arg Leu Ile Ser Arg Lys Tyr Asp Ile Gln Ser Ser Thr Leu Pro
225                 230                 235                 240

Ala Gly Leu Tyr Ala Leu Asn Gly Thr Leu Asn Ala Ala Thr Phe Glu
                245                 250                 255

Gly Ser Leu Ser Glu Val Glu Ser Leu Thr Tyr Asn Ser Leu Met Ser
                260                 265                 270

Leu Thr Thr Asn Pro Gln Asp Lys Val Asn Asn Gln Leu Val Thr Lys
                275                 280                 285

Gly Val Thr Val Leu Asn Leu Pro Thr Gly Phe Asp Lys Pro Tyr Val
                290                 295                 300

Arg Leu Glu Asp Glu Thr Pro Gln Gly Leu Gln Ser Met Asn Gly Ala
305                 310                 315                 320

Lys Met Arg Ser Thr Ala Ala Ile Ala Pro Arg Arg Tyr Glu Ile Asp
                325                 330                 335

Leu Pro Ser Gln Arg Leu Pro Val Thr Ala Thr Gly Ala Leu Thr
                340                 345                 350

Thr Leu Tyr Glu Gly Asn Ala Asp Ile Val Asn Ser Thr Thr Val Thr
                355                 360                 365

Gly Asp Ile Asn Phe Ser Leu Ala Glu Gln Pro Ala Val Glu Thr Lys
                370                 375                 380

Phe Asp Lys Lys Lys Ala Lys Lys Gln Leu Ile Asn
385                 390                 395
```

<210> SEQ ID NO 9
<211> LENGTH: 482
<212> TYPE: PRT
<213> ORGANISM: Artificial sequence
<220> FEATURE:
<223> OTHER INFORMATION: Synthetic

<400> SEQUENCE: 9

```
Met Ser Val Glu Phe Tyr Asn Ser Asn Lys Ser Ala Gln Thr Asn Ser
1               5                   10                  15

Ile Thr Pro Ile Ile Lys Ile Thr Asn Thr Ser Asp Ser Asp Leu Asn
            20                  25                  30

Leu Asn Asp Val Lys Val Arg Tyr Tyr Tyr Thr Ser Asp Gly Thr Gln
        35                  40                  45

Gly Gln Thr Phe Trp Cys Asp His Ala Gly Ala Leu Leu Gly Asn Ser
    50                  55                  60

Tyr Val Asp Asn Thr Ser Lys Val Thr Ala Asn Phe Val Lys Glu Thr
65                  70                  75                  80

Ala Ser Pro Thr Ser Thr Tyr Asp Thr Tyr Leu Asp Pro Ser His Met
                85                  90                  95

Gln Tyr Ile Lys Ala Asn Ser Lys Phe Ile Gly Ile Thr Glu Leu Ile
            100                 105                 110

Met Leu Ser Glu Ile Lys Gly Val Ile Val His Arg Leu Gly Gly Val
        115                 120                 125

Ile Met Asn Thr Asn Lys Ala Thr Ala Thr Tyr Leu Lys Ser Ile Met
    130                 135                 140

Leu Pro Glu Thr Gly Pro Ala Ser Ile Pro Asp Asp Ile Thr Glu Arg
145                 150                 155                 160

His Ile Leu Lys Gln Glu Thr Ser Ser Tyr Asn Leu Glu Val Ser Glu
                165                 170                 175

Ser Gly Ser Gly Ile Leu Val Ser Phe Pro Gly Ala Pro Gly Ser Arg
            180                 185                 190

Ile Gly Ala His Tyr Arg Trp Asn Ala Asn Gln Thr Gly Leu Glu Phe
        195                 200                 205

Asp Gln Trp Leu Glu Thr Ser Gln Asp Leu Lys Lys Ala Phe Asn Tyr
    210                 215                 220

Gly Arg Leu Ile Ser Arg Lys Tyr Asp Ile Gln Ser Ser Thr Leu Pro
225                 230                 235                 240

Ala Gly Leu Tyr Ala Leu Asn Gly Thr Leu Asn Ala Ala Thr Phe Glu
                245                 250                 255

Gly Ser Leu Ser Glu Val Glu Ser Leu Thr Tyr Asn Ser Leu Met Ser
            260                 265                 270

Leu Thr Thr Asn Pro Gln Asp Lys Val Asn Asn Gln Leu Val Thr Lys
        275                 280                 285

Gly Val Thr Val Leu Asn Leu Pro Thr Gly Phe Asp Lys Pro Tyr Val
    290                 295                 300

Arg Leu Glu Asp Glu Thr Pro Gln Gly Leu Gln Ser Met Asn Gly Ala
305                 310                 315                 320

Lys Met Arg Ser Thr Ala Ala Ile Ala Pro Arg Arg Tyr Glu Ile Asp
                325                 330                 335

Leu Pro Ser Gln Arg Leu Pro Pro Val Thr Ala Thr Gly Ala Leu Thr
            340                 345                 350

Thr Leu Tyr Glu Gly Asn Ala Asp Ile Val Asn Ser Thr Thr Val Thr
        355                 360                 365

Gly Asp Ile Asn Phe Ser Leu Ala Glu Gln Pro Ala Val Glu Thr Lys
    370                 375                 380

Phe Asp Lys Lys Lys Ala Lys Lys Gln Leu Ile Met Asn Lys Ser
385                 390                 395                 400

Asp Leu Ile Asp Ala Met Ser Ala Ser Ala Gly Ile Thr Lys Ala Ala
                405                 410                 415
```

-continued

```
Ala Lys Leu Ala Leu Glu Ser Phe Leu Gly Asn Ile Glu Glu Thr Leu
            420                 425                 430

Gln Lys Gly Gly Arg Val Ser Leu Val Gly Phe Gly Ser Trp Ser Val
        435                 440                 445

Ser Asn Arg Ala Ala Arg Asp Gly Arg Asn Pro Gln Thr Gly Ala Thr
    450                 455                 460

Ile Lys Ile Ala Ala Lys Asn Val Val Lys Phe Lys Ala Gly Ala Glu
465                 470                 475                 480

Leu Glu

<210> SEQ ID NO 10
<211> LENGTH: 15
<212> TYPE: PRT
<213> ORGANISM: Flavobacterium paraogurii

<400> SEQUENCE: 10

Leu Ser Glu Ile Lys Gly Val Ile Val His Arg Leu Glu Gly Val
1               5                   10                  15

<210> SEQ ID NO 11
<211> LENGTH: 9
<212> TYPE: PRT
<213> ORGANISM: Artificial Sequence
<220> FEATURE:
<223> OTHER INFORMATION: VP2-fused peptide

<400> SEQUENCE: 11

Lys Lys Lys Ala Lys Lys Lys Gln Leu
1               5

<210> SEQ ID NO 12
<211> LENGTH: 15
<212> TYPE: PRT
<213> ORGANISM: Clostridium tetani

<400> SEQUENCE: 12

Gln Tyr Ile Lys Ala Asn Ser Lys Phe Ile Gly Ile Thr Glu Leu
1               5                   10                  15
```